United States Patent [19]

Nishizawa et al.

[11] Patent Number: 4,859,307

[45] Date of Patent: * Aug. 22, 1989

[54] ELECTROCHEMICAL GAS SENSOR, AND METHOD FOR MANUFACTURING THE SAME

[75] Inventors: Hitoshi Nishizawa, Iwakura; Kazuyoshi Shibata, Nagoya, both of Japan

[73] Assignee: NGK Insulators, Ltd., Nagoya, Japan

[*] Notice: The portion of the term of this patent subsequent to Apr. 25, 2006 has been disclaimed.

[21] Appl. No.: 92,206

[22] Filed: Sep. 2, 1987

[30] Foreign Application Priority Data

Sep. 5, 1986 [JP] Japan ................................ 61-210432

[51] Int. Cl.$^4$ ............................................. G01N 27/46
[52] U.S. Cl. ..................................... 204/425; 204/426; 204/427; 204/429; 264/61
[58] Field of Search ....................... 204/1 S, 421-429

[56] References Cited

U.S. PATENT DOCUMENTS

| | | | |
|---|---|---|---|
| 4,502,939 | 3/1985 | Holtelder et al. | 204/425 |
| 4,579,643 | 4/1986 | Mase et al. | 204/425 |
| 4,645,572 | 2/1987 | Nishizawa et al. | 204/425 |
| 4,772,376 | 9/1988 | Yukawa et al. | 204/425 |

OTHER PUBLICATIONS

Laid-Open Publication No. 59-163558 (Japanese Pat. Appln. 58-37282).
Laid-Open Publication No. 58-19554 (Japanese Pat. Appln. No. 56-117407).
Laid-Open Publication No. 60-13256 (Japanese Pat. Appln. No. 58-121264).

Primary Examiner—T. Tung
Attorney, Agent, or Firm—Arnold, White & Durkee

[57] ABSTRACT

A gas sensor for dealing with a measurement gas in an external space, including an electrochemical pumping cell having a planar solid electrolyte body, and a first and a second electrode which are disposed on opposite surfaces of the solid electrolyte body. The sensor has a gas-tight ceramic body cooperating with the solid electrolyte body, to define therebetween a thin flat space, such that the first electrode communicates with the thin flat space. The thin flat space extends in a direction parallel to a plane of the planar solid electrolyte body and has a predetermined diffusion resistance to the measurement gas. The sensor further includes a porous structure exposed to the thin flat space in a direction of thickness of the thin flat space. The porous structure is juxtaposed with respect to the first electrode in the direction parallel to the plane of the solid electrolyte body, and maintains the thin flat space in communication with the external space under a predetermined diffusion resistance. A method of manufacturing the gas sensor is also disclosed.

16 Claims, 5 Drawing Sheets

ELECTROCHEMICAL GAS SENSOR, AND METHOD FOR MANUFACTURING THE SAME

BACKGROUND OF THE INVENTION

1. Field of the Invention

The present invention relates generally to a gas sensor which uses a solid electrolyte for determining the concentration of a component in a gaseous fluid, and a method of manufacturing the same, and more particularly to such a gas sensor which is capable of stably providing a characteristic curve for high sensing accuracy, and a method for manufacturing the same.

2. Discussion of the Prior Art

There has been known a device which incorporates an electrochemical cell using a solid electrolyte. For example, such an electrochemical device is used as an oxygen sensor having an electrochemical cell which consists of an oxygen-ion conductive solid electrolyte such as zirconia ceramics, and a pair of porous electrodes, for determining the concentration of oxygen in an exhaust gas produced by an internal combustion engine of a motor vehicle. In this type of sensor, an electrochemical pumping action is performed based on the reaction of the electrodes which occurs while an electric current is applied between the electrodes. In the meantime, one of the porous electrodes is held in communication with a measurement gas in an external space, via suitable diffusion resistance means such as a pin hole, a thin flat space or a porous ceramic layer, which provides a predetermined diffusion resistance to a flow of the measurement gas. The sensor provides an output in the form of a pumping current which corresponds to the oxygen concentration of the external measurement gas. Also known are electrochemical devices or gas sensors or detectors adapted to detect hydrogen, carbon dioxides, fuel gases, etc., by utilizing the principle based on the electrochemical pumping action and the diffusion resistance, as practiced in the oxygen sensor indicated above.

In a gas sensor using such an electrochemical cell (pumping cell) capable of performing an electrochemical pumping action, the measurement gas undergoes bulk diffusion through the diffusion-resistance means if this means consists of a pin hole or a thin flat space, or alternatively undergoes Knudsen diffusion if the diffusion-resistance means consists of a porous ceramic layer. In the former case, the gas sensor considerably suffers from a problem that a limit current obtained by the cell depends largely on the temperature of the sensor. In the latter case, the temperature dependency of the limit current tends to be a negative value, and the diffusion resistance of the porous ceramic layer depends largely on the pressure of the measurement gas. Further, the sensor using the porous ceramic layer tends to have a local variation in the diffusion resistance, due to a local variation in the porosity or size of the pores (voids) or presence of local cracks, whereby the distribution of concentration of a desired component of the measurement gas adjacent to the inner electrode is varied from one location on the electrode to another. Thus, the characteristic curve (pumping current-pumping voltage curve) to be obtained tends to be dull, leading to insufficient sensing accuracy of the gas sensor.

There is also known a gas sensor which utilizes a porous ceramic layer whose pore diameter is adjusted so that the measurement gas undergoes both the molecular diffusion and the Knudsen diffusion through the porous diffusion-resistance structure, whereby the temperature dependency of the limit current is reduced. However, the adjustment of the diameter of the pores of the porous structure may cause an undesirable change in the diffusion resistance of the porous structure, and consequently a considerable variation in the limit current obtained.

It is considered possible to construct the gas sensor such that one of the electrodes of the electrochemical pumping cell is exposed to a comparatively large internal space or cavity formed within the interior of the cell, while the internal space is held in communication with the external measurement-gas space through the diffusion-resistance means in the form of a pin hole filled with a porous body. In such a gas sensor, however, the internal space may be a useless or undesirable space. Namely, it takes a longer time for the atmosphere within the internal space to be changed according to a change in the measurement gas in the external measurement-gas space, and the operating response of the sensor is thus deteriorated. Another problem of the gas sensor of the type indicated above lies in that the concentration of the measurement gas within the internal space is fluctuated due to flows of the gas when the pressure of the measurement gas in the external space is periodically changed. In this instance, the sensing accuracy of the sensor is lowered.

Laid-open Publication Nos. 58-19554 and 60-13256 (published in 1983 and 1985, respectively) of Japanese Patent Applications disclose another type of gas sensor, in which an air gap formed around one of the two electrodes of the electrochemical pumping cell communicates with the external measurement-gas space, via a porous diffusion layer or a porous sputtered ceramic layer. Since the porous layer is formed face to face with the electrode, the thickness of the air gap may be reduced between the porous layer and the electrode, which may cause an innegligible diffusion resistance and a consequent gradient in the concentration of the introduced measurement gas on the electrode, thereby preventing the sensor from obtaining a sharp characteristic curve for accurate measurement of the concentration. If the case where the presence of the porous layer does not significantly reduce the thickness of the air gap, or the diffusion resistance provided by the gap is negligible, the air gap may be an unnecessary space that deteriorates the operating response of the sensor.

Laid-open Publication No. 59-163558 (published in 1984) of Japanese Patent Application discloses a gas sensor in which a thin flat space to which one of the electrodes of the electrochemical pumping cell is exposed communicates with the external measurement-gas space, through a porous body which defines an end of the thin flat space, so that the measurement gas diffuses through the porous body into the thin flat space. This arrangement suffers from a low limit current and a low S/N ratio. In addition, since the cross section of the porous body part which forms an inlet of the thin flat space is relatively small, the atmosphere within the thin flat space is easily affected by a local plugging of the porous body, and the porous body is difficult to be formed with consistent porosity.

SUMMARY OF THE INVENTION

The present invention was made in the light of the foregoing situations of the prior art. It is therefore a first object of the present invention to provide an improved gas sensor which uses a porous structure in combination with a thin flat space, so as to provide a sharp characteristic curve for enhanced sensing accuracy, increased durability and improved operating response.

It is a second object of the present invention to provide a method of manufacturing such an improved gas sensor.

The first object may be achieved according to the principle of the present invention, which provides a gas sensor for dealing with a measurement gas in an external space, comprising: (a) an electrochemical pumping cell including a first planar solid electrolyte body, and a first and a second electrode which are disposed on opposite surfaces of the first planar solid electrolyte body; (b) a gas-tight ceramic body cooperating with the first planar solid electrolyte body, to define therebetween a thin flat space, such that the first electrode substantially communicates with the thin flat space, the thin flat space extending in a direction parallel to a plane of the first planar solid electrolyte body and having a first predetermined diffusion resistance to the measurement gas; and (c) a porous structure exposed to the thin flat space in a direction of thickness of the thin flat space, and juxtaposed with respect to the first electrode in the direction parallel to the plane of the first planar solid electrolyte body. The porous structure has a second predetermined diffusion resistance to the measurement gas, and is adapted to maintain the thin flat space in communication with the external space, under the second predetermined diffusion resistance.

In the gas sensor of the present invention constructed as described above, the porous structure is not positioned face to face with the first electrode of the electrochemical pumping cell which substantially communicates with the thin flat space. Namely, the porous structure is juxtaposed with respect to the first electrode in the direction parallel to the first planar solid electrolyte body or the thin flat space, such that the porous structure does not overlap the first electrode, as viewed in the direction perpendicular to the plane of the first planar solid electrolyte body. Therefore, the atmosphere within the thin flat space adjacent to the first electrode is not readily affected by a local variation in the diffusion resistance of the porous structure due to local voids or cracks. In other words, the concentration of the measurement gas adjacent to the first electrode is likely to have a reduced gradient, thereby enabling the gas sensor to stably provide a sharp characteristic curve for accurate detection of the measurement gas. Further, the porous structure is exposed to the thin flat space in the direction of thickness of the space, that is, adapted to define a relatively large area of at least one of the opposite surfaces which define the thickness of the thin flat space. This arrangement is effective to minimize an influence of local plugging or clogging of the porous structure on the sensing capability of the gas sensor.

According to one advantageous feature of the invention, the porous structure fills an aperture formed in the first planar solid electrolyte body and/or the gas-tight ceramic body, and the porous structure is co-fired, together with the solid electrolyte body and/or the ceramic body which has (have) the aperture filled with the porous structure. In this case, each porous structure is supported by the solid electrolyte body or ceramic body, as an integral part thereof, and the thus integrally co-fired gas sensor is provided with an increased mechanical strength and excellent durability at elevated temperatures.

According to the invention, the volume of the thin flat space is preferably no more than 70% of a sum of the volume of the thin flat space and the volume of the porous structure, in order to avoid deterioration of the operating response of the sensor due to an excessively large volume of the thin flat space, and to prevent lowering of the measuring accuracy of the sensor due to a periodic pressure fluctuation of the measurement gas.

The thin flat space to which the first electrode is exposed, and the porous structure for communication between the thin flat space and the external measurement-gas space, have the specific diffusion resistance values, which are suitably determined so as to reduce the dependency of the sensor output upon the temperature of the sensor and the pressure of the measurement gas. In other words, the temperature and pressure dependency of the sensor can be readily adjusted, by properly adjusting the diffusion resistance values of the thin flat space and the porous structure, since the measurement gas is adapted to undergo both bulk diffusion through the thin flat space, and diffusion through the porous structure. To minimize the temperature and pressure dependency of the sensor, it is desirable to hold the first diffusion resistance of the thin flat space within a range between 2% and 50%, preferably, between 5% and 20% of an overall diffusion resistance which is a sum of the first diffusion resistance, and the second diffusion resistance of the porous structure.

In the gas sensor of the invention, the concentration of a desired component in the measurement gas is determined according to the principle based on the diffusion resistance to the molecules of the component, and based on an electrochemical pumping of ions of the component through the first planar solid electrolyte body between the first and second electrodes of the electrochemical pumping cell, upon application of an electric current between these two electrodes. However, it is possible to provide the gas sensor with another electrochemical cell (electrochemical sensing cell), which is operated according to the principle of a concentration cell, for detecting the atmosphere adjacent to the first electrode of the pumping cell which communicates with the external measurement-gas space through the thin flat space and the porous structure. This electrochemical cell provided in addition to the electrochemical pumping cell includes a second planar solid electrolyte body, and a third and a fourth electrode which are formed on the second planar solid electrolyte body, such that the third electrode substantially communicates with the thin flat space. This arrangement having the two electrochemical cells described above is advantageous for widening the range of applications of the sensor, i.e., one of preferred embodiments of the present invention.

In the case where the second electrochemical cell is provided, the second planar solid electrolyte body may constitute at least a portion of the gas-tight ceramic body which partially defines the thin flat space. Alternatively, the second planar solid electrolyte body may constitute a portion of the first planar solid electrolyte body. In either case, it is preferred that the third electrode be spaced from the porous structure in the direction parallel to the plane of the solid electrolyte bodies, by a larger distance than the first electrode.

According to a still further advantageous feature of the invention, the porous structure is a laminar structure consisting of a plurality of porous layers having different porosities. The porous layers are superposed on each other in the direction of thickness of the thin flat space. In this instance, the external measurement gas diffuses through the porous layers successively, and reaches the thin flat space. Alternatively, the porous structure may be a laminar structure consisting of a plurality of porous layers which are superposed on each other in the direction of thickness of the thin flat space and which have at least one air gap between the adjacent layers. In this case, the flows of the measurement gas diffusing through the porous layers may be mixed together in the air gap, for even distribution of the measurement gas.

In accordance with a yet further advantageous feature of the invention, the porous structure, the thin flat space and the first electrode have a columnar or cylindrical shape, a disc-like shape, and an annular shape, respectively. In this case, the annular electrode is preferably disposed radially outwardly of the columnar porous structure, namely, the porous structure is positioned within an opening of the annular first electrode.

According to another preferred feature of the invention, the porous structure is formed of a material whose major component is the same as a major component of a material of which the first planar solid electrolyte body or the ceramic body is formed. In this instance, the sensor has an increased constructional strength.

According to still another feature of the invention, the porous structure is a one-piece ceramic boy which consists of a protrusion filling an aperture formed in the first planar solid electrolyte body, and a protective layer having a predetermined thickness covering the second electrode disposed on the first planar solid electrolyte body.

The second object of the invention may be attained according to another aspect of the invention, which provides a method of manufacturing the gas sensor of the invention, comprising the steps of: (1) preparing a first green sheet which gives the first planar solid electrolyte body, and a second green sheet which gives the gas-tight ceramic plate, and forming an aperture in at least one of the first and second green sheets; (2) forming a ceramic green body which gives the porous structure, and inserting the formed ceramic green body into the aperture formed in each of the above-indicated at least one of the first and second green sheets; and (3) superposing the first and second green sheets one on the other, pressing the superposed first and second green sheets toward each other under heat, and firing the pressed first and second green sheets into a fired one-piece structure.

Alternatively, the gas sensor of the invention may be manufactured by a method which comprises the steps of: (1') preparing a first green sheet which gives the first planar solid electrolyte body, and a second green sheet which gives the gas-tight ceramic plate, and forming an aperture in at least one of the first and second green sheets; (2') preparing a ceramic paste which gives the porous structure, and filling the aperture formed in each of the above-indicated at least one of the first and second green sheets, with the ceramic paste; and (3') superposing the first and second green sheets one on the other, pressing the superposed first and second green sheets toward each other under heat, and firing the pressed first and second green sheets into a fired one-piece structure.

BRIEF DESCRIPTION OF THE DRAWINGS

The above and optional objects, features and advantages of the present invention will become more apparent by reading the following detailed description of presently preferred embodiments of the invention, when considered in connection with the accompanying drawings, in which.

DETAILED DESCRIPTION OF THE PREFERRED EMBODIMENTS

To further clarify the present invention, the several presently preferred embodiments of the invention will be described in detail, by reference to the accompanying drawings.

Figure 1:
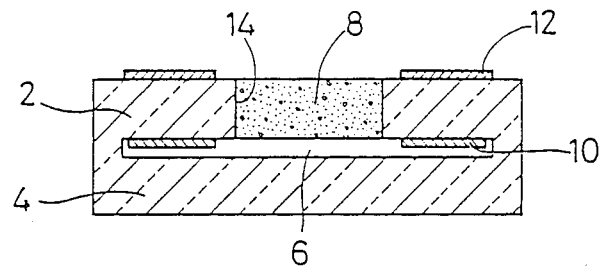
FIGS. 1 and 2 are elevational views in transverse cross section of the most simple examples of construction of a gas sensor according to the present invention.

Referring first to the transverse cross sectional view of FIG. 1, there is shown an example of one of basic constructions of a gas sensor in the form of an oxygen sensor according to the principle of the present invention. In this illustrated construction of the oxygen sensor, a planar body 2 of a solid electrolyte such as a zirconia ceramic, and a gas-tight or dense ceramic plate 4 made of a ceramic material similar to that of the planar solid electrolyte body 2, are formed as an integral structure, such that the planar solid electrolyte body 2 is superposed on the dense ceramic plate 4, such that a circular or disc-like thin flat space 6 having a relatively small thickness selected to provide a predetermined diffusion resistance to a gaseous fluid is formed as an internal space between the solid electrolyte body 2 and the ceramic plate 4. This thin flat internal space 6 is separated from an external space.

An annular first electrode 10 is formed on one of opposite surfaces, i.e., inner surface of the planar solid electrolyte body 2 which defines a part of the thin flat space 6. An annular second electrode 12 is formed on the other surface, i.e., outer surface of the solid electrolyte body 2, in coaxial relation with the annular first electrode 10. The solid electrolyte body 2, and the annular first and second electrodes 10, 12 constitute an electrochemical pumping cell.

An aperture 14 having suitable dimensions is formed through a portion of the planar solid electrolyte body 2 which is located radially inwardly of the annuli of the annular first and second electrodes 10, 12, such that the aperture 14 is open to a central portion of the circular thin-flat space 6. This aperture 14 is filled with a columnar or cylindrical porous layer 8 which has a predetermined diffusion resistance. The columnar porous layer 8 is formed as an integral part of the solid electrolyte body 2. The porous layer 8 is juxtaposed with respect to the first electrode 10, in a direction parallel to the plane of the thin flat space 6 (upper and lower surfaces in FIG. 1, which define the thickness of the thin flat space 6). In other words, the porous layer 8 does not overlap the first electrode 10, as viewed in the direction perpendicular to the plane of the thin flat space 6.

Six different specimens 1–6 of a gas sensor according to the basic construction described above were produced, as specified in Table 1. In all the specimens 1–6, the thin flat space 6 has a diameter of 5.0 mm, and the first electrode 10 has an inside diameter of 2.5 mm, while the porous layer 8 has a thickness of 0.5 mm. The overall limit current in the table was measured with the aperture 14 being filled with the porous layer 8, in a gaseous fluid having an $O_2$ content of 2% and an $N_2$ content of 98%, at a temperature of the sensor of 700° C. at one (1) atmospheric pressure of the gaseous fluid. The limit current of the thin flat space 6 was measured under the same condition as specified above, after the porous layer 8 was removed with a diamond tool. The limit current % is a percentage of the overall limit current with respect to the limit current of the thin flat space 6, i.e. a percentage of the diffusion resistance of the thin flat space 6 with respect to the overall diffusion resistance of the porous layer 8 and the thin flat space 6. The temperature dependency % indicates a change in the overall limit current, when the sensor temperature was raised from 700° C. to 800° C. The pressure dependency % indicates a change in the overall limit current, when the pressure of the gaseous fluid was raised from 0.5 atmospheric atmosphere to 1.0 atmospheric atmosphere.

contact between the porous layer 8 and the thin flat space 6, since the entire inner surface of the porous layer 8 is exposed to the thin flat space 6, in other words, the thin flat space 6 is partly defined by the porous layer 8. Therefore, the instant arrangement is less likely to be affected by a local clogging or plugging of the porous layer 8. Further, the porous layer 8 is not disposed face to face with the first electrode 10, i.e., juxtaposed in spaced-apart relation with the first electrode 10. This arrangement is therefore less likely to be affected by a variation in the diffusion resistance of the porous layer 8 from one area to another due to local voids or cracks. Accordingly, the present arrangement reduces a possibility that there arises an abnormal variation in the oxygen concentration of the measurement gas near the first electrode 10. Hence, the electrochemical cell (2, 10, 12) is capable of stably providing a polarization characteristic curve for accurate measurement of the oxygen concentration.

Thus, the diffusion of the measurement gas through the porous layer 8 is uniquely combined with the bulk diffusion through the thin flat space 6, so that the temperature and pressure dependencies of the oxygen sensor may be easily adjusted. In particular, since there exists a reduced useless volume near the first electrode 10 located in the portion of the diffusion-resistance means (thin flat space 6) remote from the porous layer 8, the atmosphere contacting the first electrode 10 is efficiently changed according to a change in the external measurement gas, and a change in the pumping current

TABLE 1

| Specimen No. | Composition of Porous Layer | Diameter (mm) of Porous Layer | Thickness (mm) of Thin Flat Space | Overall Limit Current (mA) | Limit Current (mA) of Thin Flat Space | Limit Current Percentage | Temperature Dependency (%) | Pressure Dependency (%) |
|---|---|---|---|---|---|---|---|---|
| 1 | $Al_2O_3$: 92 wt % $SiO_2$: 5 wt % MgO: 1 wt % | 2.0 | 0.050 | 0.45 | 23 | 2.0 | −2.1 | 69 |
| 2 | $Al_2O_3$ | 2.0 | 0.015 | 0.28 | 5.5 | 5.1 | −0.7 | 65 |
| 3 | $Al_2O_3$: 61 wt % $ZrO_2$: 29 wt % | 1.5 | 0.008 | 0.21 | 1.4 | 15 | 0.4 | 50 |
| 4 | $ZrO_2$ | 1.0 | 0.030 | 0.54 | 2.8 | 19 | 1.7 | 35 |
| 5 | $Al_2O_3$: 22 wt % $ZrO_2$: 78 wt % | 1.0 | 0.020 | 1.04 | 2.1 | 50 | 3.0 | 38 |
| 6 | $ZrO_2$ | 0.5 | 0.012 | 0.46 | 0.70 | 66 | 5.2 | 15 |

Figure 2:
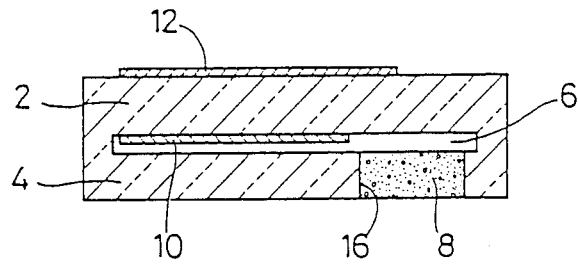

Another construction of the oxygen sensor of the present invention is shown in FIG. 2, wherein rectangular first and second electrodes 10, 12 are formed on the opposite surfaces of the planar solid electrolyte body 2, so that the electrodes 10, 12 cooperate with the solid electrolyte body 2 to constitute an electrochemical pumping cell. In this arrangement, the thin flat space 6 formed between the solid electrolyte body 2 and the dense ceramic plate 4 has also a rectangular configuration, and the porous layer 8 is accommodated in an aperture 16 formed through the ceramic plate 4. The porous layer 8 is juxtaposed with respect to the first electrode 10, in a direction parallel to the plane of the thin flat space 6 (upper and lower surfaces in FIG. 1, which define the thickness of the thin flat space 6).

According to the illustrated constructions of the oxygen sensor described above, the gaseous fluid or external measurement gas existing in an external space is introduced into the thin flat space 6 through the porous layer 8, under the predetermined diffusion resistance. The introduced measurement gas diffuses within the thin flat space 6, in the direction of the plane of the space 6 (right and left direction in FIGS. 1 and 2), to the first electrode 10. There is a relatively large area of due to a pressure pulsation of the measurement gas is reduced, whereby the operating response of the sensor is improved, and the oxygen concentration of the measurement gas is accurately determined.

Further, the present oxygen sensor has a relatively high mechanical strength and is highly durable at an elevated temperature in particular, since the porous layer 8 is supported by the solid electrolyte body 2 or dense ceramic plate 4, and is integrally co-fired with these members.

In the present gas sensor, a DC current from an external power source is applied between the first and second electrodes 10, 12 of the electrochemical pumping cell, as is well known in the art, so that ions of a component of the measurement gas (oxygen ions in the illustrated examples) are moved from the first electrode 10 to the second electrode 12, or vice versa, whereby the component diffuses through the porous layer 8 and the thin flat space 6 from the external measurement-gas space and reaches the first electrode 10. The concentration of the component whose ions are moved between the electrodes 10, 12, or the concentration of a component which chemically reacts with the diffused component, is detected in an ordinary manner, by means of an ammeter or a potentiometer.

The gas sensor of the present invention is by no means limited to the above-illustrated constructions, but the principle of the invention may be effectively embodied as the gas sensor having modified constructions as illustrated in FIGS. 3 through 6.

Figure 3:
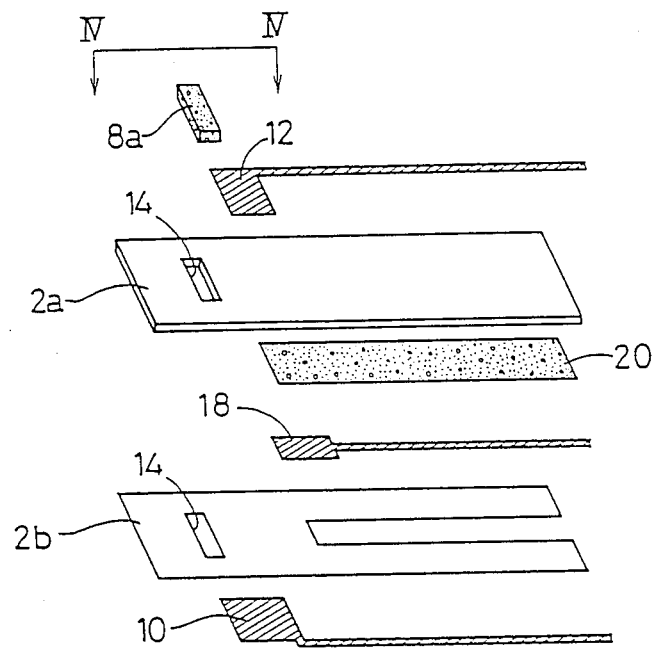
FIGS. 3 and 5 are perspective views of other examples of the gas sensor according to the invention.
Figure 3:
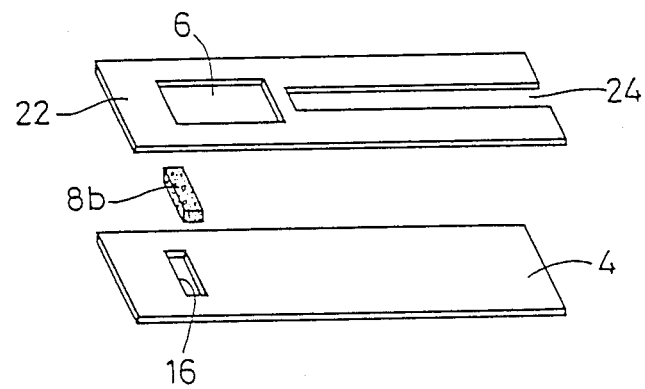
Figure 4:
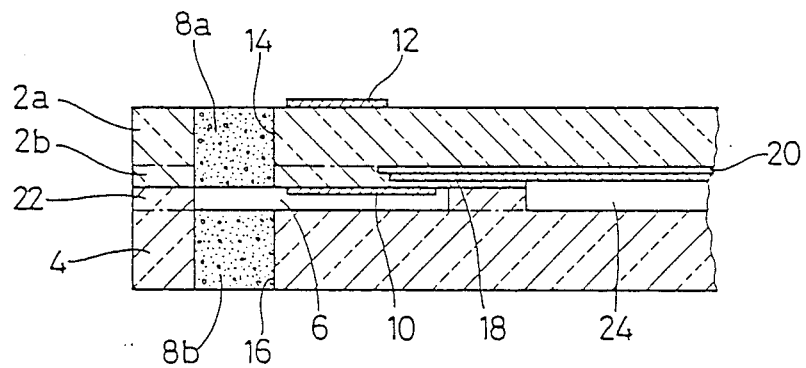
FIGS. 4 and 6 are elevational views in cross section, taken along lines IV—IV of FIG. 3 and lines VI—VI of FIG. 5, respectively.

A first modified gas sensor of FIGS. 3 and 4 is characterized in that the sensor has an electrochemical sensing cell in addition to an electrochemical pumping cell. This sensor has two solid electrolyte plates $2a$, $2b$ superposed on each other as a planar solid electrolyte body. On the opposite surfaces of this solid electrolyte body, there are formed the first and second electrodes 10, 12, whereby the electrochemical pumping cell is constituted. Further, the electrochemical sensing cell is constituted by the solid electrolyte plate $2b$, and the first electrode 10 and a fourth electrode 18 which are formed on the opposite surfaces of the solid electrolyte plate $2b$.

Described more specifically, the fourth electrode 18 and a porous insulating layer 20 made of alumina, for example, are interposed between the two solid electrolyte plates $2a$, $2b$, such that the fourth electrode 18 is sandwiched between the porous alumina insulating layer 20 and the solid electrolyte plate $2b$, and such that the fourth electrode 18 partially overlaps the first electrode 10 as seen in a plane parallel to the planes of the solid electrolyte plates $2a$, $2b$. Thus, the electrochemical sensing cell is formed. In the instant sensor, the first electrode 10 serves not only as one of the two electrodes of the electrochemical pumping cell, but also as one of the two electrodes of the electrochemical sensing cell, i.e., as a third electrode which cooperates with the fourth electrode 18.

The fourth electrode 18 communicates with an air passage 24 which is defined by a gas-tight or dense ceramic spacer member 22 formed on the solid electrolyte plate $2b$, and the ceramic plate 4. An ambient air is introduced as a reference gas into the air passage 24 through an open end of the passage 24 at a proximal end of the spacer member 22. The fourth electrode 18 functions as a reference electrode which is exposed to the reference ambient air introduced in the air passage 24. On the other hand, the first electrode 10 communicates with the thin flat space 6, so that the first electrode 10 functions as a measuring electrode of the electrochemical sensing cell, which cooperates with the fourth electrode 18 to detect a concentration of a component of the atmosphere within the thin flat space 6.

As is apparent from FIG. 4, the present sensor has two porous layers $8a$, $8b$ which are accommodated in respective apertures 14, 16 formed in the solid electrolyte body $2a$, $2b$ and the ceramic plate 4, respectively, such that the two porous layers $8a$, $8b$ are disposed in opposed relation with each other. The measurement gas existing in the external measurement-gas space is introduced into the thin flat space 6, through these two porous layers $8a$, $8b$, under a predetermined diffusion resistance. The introduced measurement gas diffuses through the thin flat space 6, so that the first electrode 10 contacts the measurement gas.

In the thus constructed sensor, a DC current is applied between the first and second electrodes 10, 12 of the electrochemical pumping cell, in order to control an atmosphere which exists adjacent to the first electrode 10, as a result of diffusion of the measurement gas through the porous layers $8a$, $8b$ and the thin flat space 6. Simultaneously, the concentration of a gaseous component of the thus controlled atmosphere adjacent to the first electrode 10 is detected or measured in a known manner by the electrochemical sensing cell. Namely, an electromotive force is induced between the first and fourth electrodes 10, 18 of the sensing cell due to a difference in the concentration of the component between the atmospheres contacting the two electrodes 10, 18. The induced electromotive force is applied to an external measuring device, which determines the concentration of the component of the measurement gas, based on the detected electromotive force.

Figure 6:
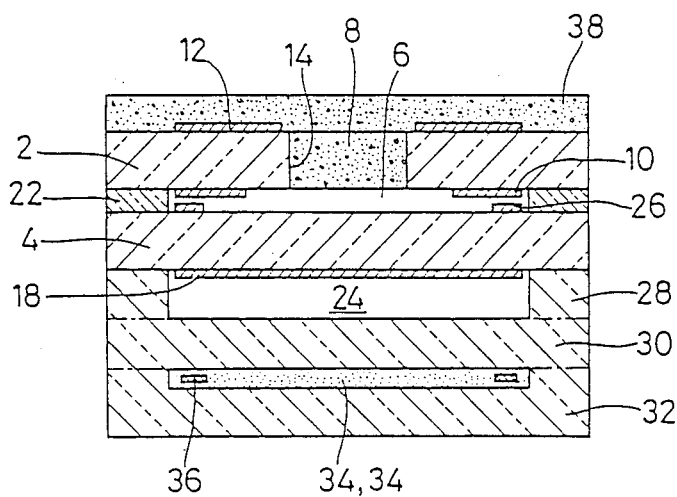
Figure 5:
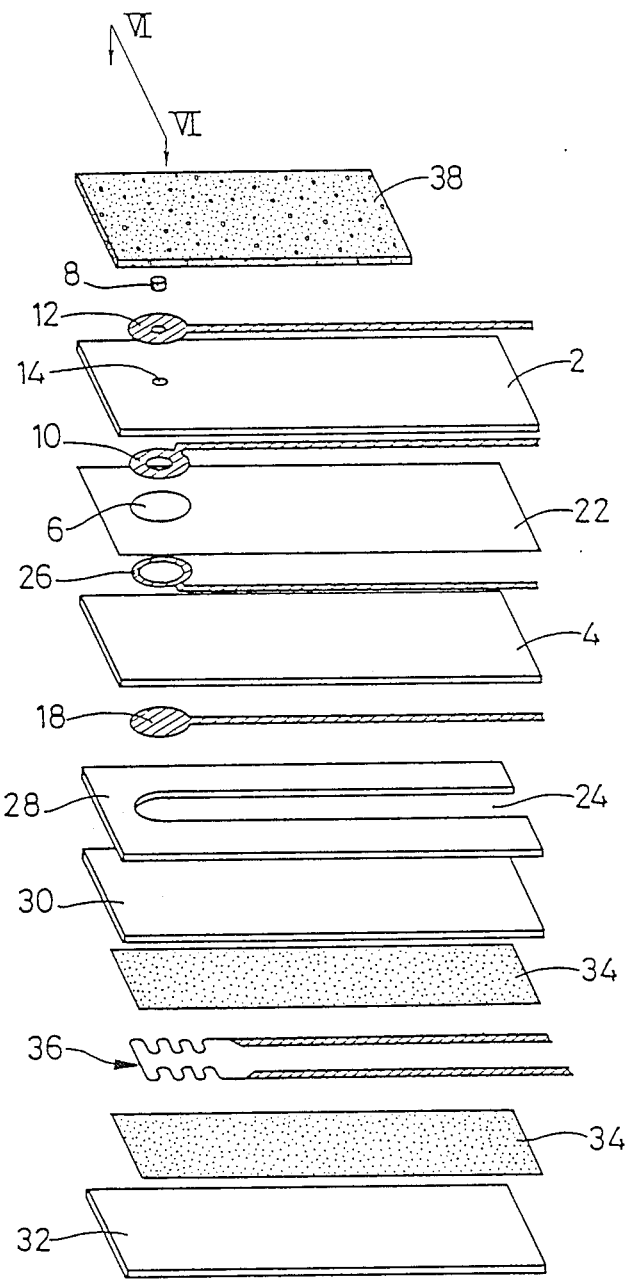

The gas sensor shown in FIGS. 5 and 6 is similar to that of FIGS. 3 and 4, in that both the electrochemical pumping cell and the electrochemical sensing cell are integrally provided. Unlike the sensor of FIGS. 3–4 wherein the portion ($2b$) of the solid electrolyte body ($2a$, $2b$) of the electrochemical pumping cell is used as the solid electrolyte body of the electrochemical sensing cell, the present sensor is adapted such that the dense ceramic body 4 consists of a planar solid electrolyte body made of zirconia or other solid electrolyte material. On the opposite surfaces of this solid electrolyte body 4, there are formed a third electrode 26 and the fourth electrode 18. The third electrode 26 and the first electrode 10 communicate with the thin flat space 6, such that these two electrodes are disposed in opposed relation with each other. Thus, the electrochemical sensing cell is constructed. Unlike the preceding embodiment in which the same electrode 10 serves commonly as the first and third electrodes, the present sensor uses the two separate electrodes 10, 26 as the first and third electrodes.

On one side of the ceramic plate 4 on which the fourth electrode 18 is disposed, there are formed a spacer member 28, a covering member 30 and a support member 32, in the order of description. These members 28, 30, 32 are formed of a dense ceramic material, each in the form of a plate. The spacer member 28 has an elongate cutout which is closed by the ceramic plate 4 and the covering member 30, so that the air passage 24 is defined by these three members 28, 4, 30. The fourth electrode 18 communicates with this air passage 24. Between the covering member 30 and the support member 32, there is provided a heater element 36 sandwiched by two electrically insulating layers 34, 34 made of alumina or similar electric resistive material. Thus, the instant sensor incorporates heating means for heating the electrochemical cells.

The second electrode 12 formed on the outer surface of the electrochemical pumping cell is covered by a porous protective layer 38, so that the second electrode 12 communicates with the measurement gas in the external measurement-gas space, through the porous protective layer 38. Thus, the second electrode 12 is protected against direct exposure to the external measurement gas.

In the thus constructed gas sensor, the measurement gas, which is introduced from the external measurement-gas space through the protective layer 38, diffuses into the thin flat space 6 through the porous layer 8, under a predetermined diffusion resistance. The measurement gas then diffuses through the thin flat space 6, under a predetermined diffusion resistance, toward the annular first electrode 10. The atmosphere adjacent to the first electrode 10 is controlled by means of a pumping action of the electrochemical pumping cell, while the concentration of a component of the thus controlled atmosphere around the first electrode 10 is detected by the electrochemical sensing cell (4, 26, 18).

In the present embodiment wherein the heater element 36 is energized by an external power source, the gas sensor or electrochemical device in the form of an oxygen sensor is heated by the energized heater element 36. Accordingly, the solid electrolyte bodies (2, 4) and the electrodes (10, 12; 26, 18) may be maintained at optimum operating temperatures, so as to assure accurate and reliable operation of the gas sensor, even while the temperature of the measurement gas is relatively low.

In the gas sensors which have been illustrated, the ion-conductive solid electrolyte used for the electrochemical pumping and sensing cells may be made of an oxygen-ion conductive solid electrolyte such as zirconia ceramics or a solid solution of $Bi_2O_3$-$Y_2O_3$, a proton-conductive solid electrolyte such as $SrCe_{0.95}Yb_{0.05}O_{3-\alpha}$, a halogen-conductive solid electrolyte such as $CaF_2$, or other known solid electrolyte materials.

The electrodes 10, 12, 18, 26 of the electrochemical cells are made of metals such as platinum, rhodium, palladium, gold and nickel, or conductive compounds such as tin oxide. Preferably, the electrodes have a porous structure. According to one preferred method of forming the electrodes, a material consisting principally of a metal or conductive compound indicated above is applied by printing to the respective solid electrolyte, and the applied material is fired into the suitably formed electrodes, and leads or conductor strips extending from the electrodes. To avoid flake-off or separation of the electrodes and their leads from the solid electrolyte bodies, or disconnection or breakage of the leads, it is desirable that the material of the electrodes and leads contains a powdered ceramic material such as zirconia, yttria or alumina, so that the fired electrodes and leads may be integrally bonded to the contacting surface of the solid electrolyte, with an increased adhesion thereto.

A green laminar structure of the gas sensors according to the present invention may be prepared in a known lamination or screen-printing process, and the prepared green laminar structure may be co-fired in a suitable process also known in the art. According to the invention, the porous layer 8 is preferably formed by a method as illustrated in FIG. 7 by way of example.

Figure 7:
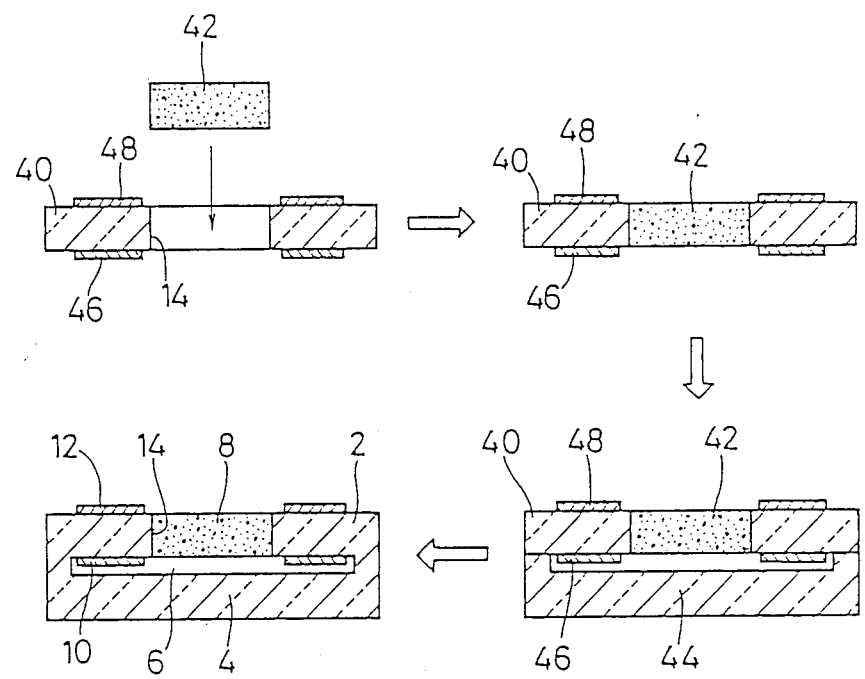
FIG. 7 is a view illustrating one form of a process for manufacturing the gas sensor of FIG. 1.

According to the method shown in FIG. 7, the aperture 14 is formed through an appropriate portion of a green sheet 40 which gives the solid electrolyte body 2, and a formed ceramic green body 42 which gives the porous layer 8 is inserted in the aperture 14. The green sheet 40 is then superposed on a green sheet 44 which gives the dense ceramic plate 4, and the two superposed green sheets 40, 44 are pressed together under heat. Subsequently, the green sheets 40, 44 are co-fired into a desired fired integral body, i.e., a gas sensing element as illustrated in FIG. 1. The above method includes a step of forming green layers 46, 48 for the electrodes 10, 12, by screen-printing, for example, on the opposite surfaces of the green sheet 40 for the solid electrolyte body 2. This step is implemented at a suitable stage of the process.

It will be understood that when the above method is applied to produce the gas sensor shown in FIG. 2, the aperture 16 is formed through the green sheet 44 which gives the dense ceramic plate 4, and the formed ceramic green body 42 is inserted in the aperture 16.

In the illustrated method of production, the preformed ceramic green body 42 is inserted into the aperture 14 or 16 formed in the green sheet 40 or 44. However, this technique may be replaced by a method in which the aperture 14, 16 is filled with a suitably prepared ceramic paste so that the paste will produce the porous layer 8 by co-firing the paste and the green sheet 40, 44.

Figure 8:
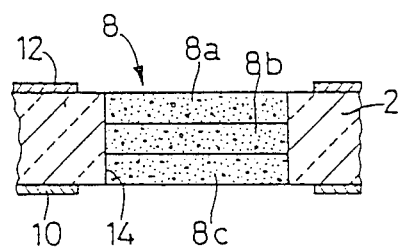
FIGS. 8 and 9 are fragmentary elevational views in cross section, showing different porous layers.
Figure 9:
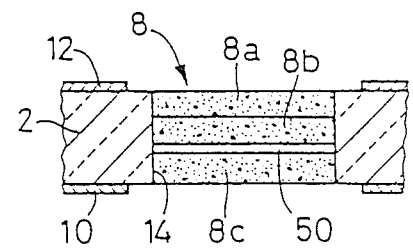

While the porous layer 8 described above consists of a single porous layer, it may be replaced by a porous structure 8 which consists of a plurality of porous layers as illustrated in FIGS. 8 and 9. The porous structure 8 of FIG. 8 consists of three porous layers 8a, 8b and 8c which have different porosities and which are superposed on each other in the direction of thickness of the thin flat space 6. The porous structure 8 of FIG. 9 also consists of the three porous layers 8a, 8b and 8c, but has a thin flat air gap 50 formed between the porous layers 8b and 8c.

The porous layer or structure 8 formed according to the present invention may be made of a ceramic material which has a sintering temperature different than that of the material of the solid electrolyte body 2 or ceramic plate 4. For example, alumina may be used for the porous layer or structure 8, when zirconia ceramics are used for the solid electrolyte body 2. However, the ceramic material used for the solid electrolyte body 2 or ceramic plate 4 may be used for the porous layer or structure 8, if the ceramic material used is mixed with a material which disappears upon firing. In this case, the bonding or adhesive strength of the porous layer or structure 8 to the solid electrolyte body 2 or ceramic plate 4 may be improved, and the porous structure 8 and the body 2 or plate 4 may exhibit the same thermal expansion characteristics, whereby their mechanical strength and durability can be effectively increased. Of course, the porous layer or structure 8 may be formed of a mixture of two different ceramic materials, i.e., alumina or other material different from the material of the solid electrolyte body 2 or ceramic plate 4, and the ceramic material used for the body 2 or plate 4.

Figure 10:
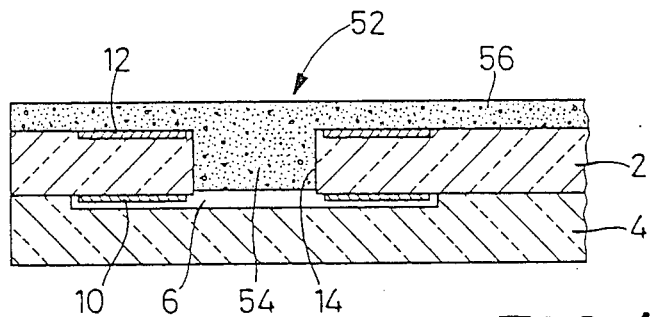
FIGS. 10 through 12 are cross sectional views showing further modified embodiments of the present invention.

Further, the porous structure used according to the invention may be an integral part of a protective layer for the second electrode 12, as illustrated in FIG. 10. Described more specifically, the gas sensor shown in FIG. 10 includes a one-piece porous ceramic body 52 which consists of a protrusion 54 filling the aperture 14 in the solid electrolyte body 2, and a protective layer 56 having a suitable thickness covering the second electrode 12.

Figure 11:
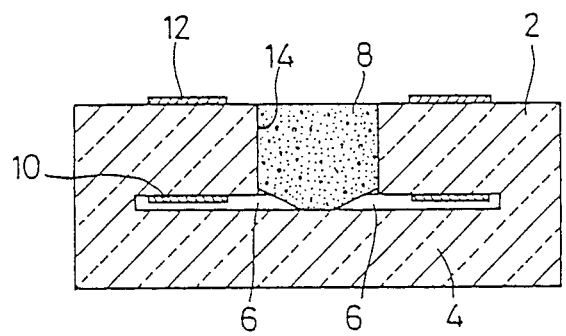
Figure 12:
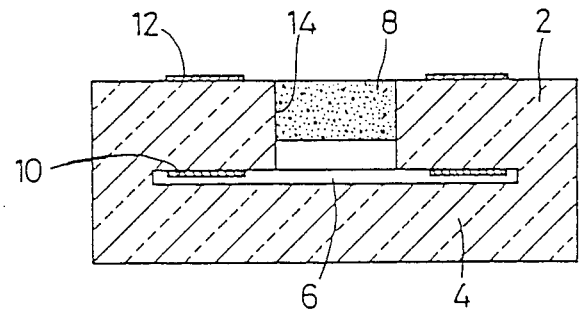

Further modified porous structures according to the invention are illustrated in FIG. 11 wherein a part of the porous structure 8 is held in abutting contact with the ceramic plate 4, and in FIG. 12 wherein the porous structure 8 fills only a portion of the volume of the aperture 14. In these cases, too, the principle of the present invention may be practiced.

While the present invention has been described in its presently preferred embodiments or examples, it is to be understood that the invention is not limited to the precise details of construction or process steps of the illustrated embodiments, but may be embodied with various changes, modifications and improvements which may occur to those skilled in the art, without departing from the spirit and scope of the invention defined in the appended claims.

Although the gas sensor according to the present invention is suitably or advantageously used as a sensor for dealing with rich-burned or lean-burned exhaust gases emitted from an engine of an automotive vehicle, the instant gas sensor may also be used as an oxygen sensor for determining the oxygen concentration of other gases such as exhaust gases produced as a result of combustion of an air-fuel mixture having a stoichiometric air/fuel ratio. Further, the instant gas sensor may be used as other sensors, detectors or controllers adapted to detect hydrogen, carbon dioxides and other components of a fluid which are associated with electrode reaction.

What is claimed is:

1. A gas sensor for dealing with a measurement gas in an external space, comprising:
    an electrochemical pumping cell including a first planar solid electrolyte body, and a first electrode and a second electrode which are disposed on opposite surfaces of said first planar solid electrolyte body;
    a gas-tight ceramic body cooperating with said first planar solid electrolyte body, to define therebetween a thin flat space, such that said first electrode substantially communicates with said thin flat space, said thin flat space extending in a direction parallel to a plane of said first planar solid electrolyte body and having a first predetermined diffusion resistance to said measurement gas; and
    a porous structure exposed to said thin flat space in a direction of thickness of said thin flat space, and juxtaposed with respect to said first electrode in said direction parallel to the plane of said first planar solid electrolyte body, said porous structure having a second predetermined diffusion resistance to said measurement gas, and maintaining said thin flat space in communication with said external space under said second predetermined diffusion resistance.

2. A gas sensor according to claim 1, wherein said porous structure fills an aperture formed in at least one of said first planar solid electrolyte body and said gas-tight ceramic body, said porous structure being co-fired with said at least one of said solid electrolyte body and said ceramic body.

3. A gas sensor according to claim 1, wherein said first diffusion resistance of said thin flat space is within a range between 2% and 50% of an overall diffusion resistance which is a sum of said first diffusion resistance and said second diffusion resistance of said porous structure.

4. A gas sensor according to claim 1, further comprising an electrochemical sensing cell including a second planar solid electrolyte body, and a third electrode and a fourth electrode which are formed on said second planar solid electrolyte body, such that said third electrode substantially communicates with said thin flat space.

5. A gas sensor according to claim 4, wherein said second planar solid electrolyte body constitutes at least a portion of said gas-tight ceramic body.

6. A gas sensor according to claim 4, wherein said second planar solid electrolyte body constitutes a portion of said first planar solid electrolyte body.

7. A gas sensor according to claim 4, wherein said third electrode is spaced from said porous structure in said direction parallel to said plane of said first planar solid electrolyte body, by a larger distance than said first electrode.

8. A gas sensor according to claim 1, wherein said porous structure is a laminar structure consisting of a plurality of porous layers which have different porosities and which are superposed on each other in said direction of thickness of said thin flat space.

9. A gas sensor according to claim 1, wherein said porous structure is a laminar structure consisting of a plurality of porous layers superposed on each other in said direction of thickness of said thin flat space, said laminar structure having at least one air gap between adjacent porous layers of said plurality of porous layers.

10. A gas sensor according to claim 1, wherein said porous structure, said thin flat space and said first electrode have a columnar, a disc and an annular shape, respectively, and said annular first electrode is disposed radially outwardly of said columnar porous structure.

11. A gas sensor according to claim 1, wherein said porous structure is formed of a material whose major component is the same as a major component of a material of which one of said first planar solid electrolyte body and said gas-tight ceramic body is formed.

12. A gas sensor according to claim 1, wherein said porous structure is a one-piece ceramic body which consists of a protrusion filling an aperture formed in said first planar solid electrolyte body, and a protective layer having a predetermined thickness covering said second electrode disposed on said first planar solid electrolyte body.

13. A gas sensor for dealing with a measurement gas in an external space, comprising:
    an electrochemical pumping cell including a first planar solid electrolyte body, and a first electrode and a second electrode which are disposed on opposite surfaces of said first planar solid electrolyte body;
    a gas-tight ceramic body cooperating with said first planar solid electrolyte body, to define therebetween a thin flat space having a thickness of not greater than about 50 microns, such that said first electrode substantially communicates with said thin flat space, said thin flat space extending in a direction parallel to a plane of said first planar solid electrolyte body and having a first predetermined diffusion resistance to said measurement gas; and
    a porous structure exposed to said thin flat space in a direction of thickness of said thin flat space, and juxtaposed with respect to said first electrode in said direction parallel to the plane of said first planar solid electrolyte body, said porous structure having a second predetermined diffusion resistance to said measurement gas, and maintaining said thin flat space in communication with said external space under said second predetermined diffusion resistance.

14. A gas sensor for dealing with a measurement gas in an external space, comprising:
    an electrochemical pumping cell including a first planar solid electrolyte body, and a first electrode and a second electrode which are disposed on opposite surfaces of said first planar solid electrolyte body;
    a gas-tight ceramic body cooperating with said first planar solid electrolyte body, to define therebetween a thin flat space such that said first electrode substantially communicates with said thin flat space, said thin flat space extending in a direction parallel to a plane of said first planar solid electrolyte body and having a first predetermined diffusion resistance to said measurement gas;

an air inlet aperture formed through said first planar solid electrolyte body in a direction of thickness of said body, said aperture providing communication between said external space and said thin flat space; and a porous structure disposed within said air inlet aperture and exposed to said thin flat space in a direction of thickness of said thin flat space, and juxtaposed with respect to said first electrode in said direction parallel to the plane of said first planar solid electrolyte body, said porous structure having a second predetermined diffusion resistance to said measurement gas, and maintaining said thin flat space in communication with said external space under said second predetermined diffusion resistance.

15. A gas sensor for dealing with a measurement gas in an external space, comprising:

an electrochemical pumping cell including a first planar solid electrolyte body, and a first electrode and a second electrode which are disposed on opposite surfaces of said first planar solid electrolyte body;

a gas-tight ceramic body cooperating with said first planar solid electrolyte body, to define therebetween a thin flat space such that said first electrode substantially communicates with said thin flat space, said thin flat space extending in a direction parallel to a plane of said first planar solid electrolyte body and having a first predetermined diffusion resistance to said measurement gas;

an air inlet aperture formed through said gas-tight ceramic body in a direction of thickness of said body, said aperture providing communication between said external space and said thin flat space; and a porous structure disposed within said air inlet aperture and exposed to said thin flat space in a direction of thickness of said thin flat space, and juxtaposed with respect to said first electrode in said direction parallel to the plane of said first planar solid electrolyte body, said porous structure having a second predetermined diffusion resistance to said measurement gas, and maintaining said thin flat space in communication with said external space under said second predetermined diffusion resistance.

16. A gas sensor for dealing with a measurement gas in an external space, comprising:

an electrochemical pumping cell including a first planar solid electrolyte body, and a first electrode and a second electrode which are disposed on opposite surfaces of said first planar solid electrolyte body;

a gas-tight ceramic body cooperating with said first planar solid electrolyte body, to define therebetween a thin flat space such that said first electrode substantially communicates with said thin flat space, said thin flat space extending in a direction parallel to a plane of said first planar solid electrolyte body and having a first predetermined diffusion resistance to said measurement gas;

air inlet apertures formed through said first planar solid electrolyte body and said gas-tight ceramic body in a direction of thickness of said bodies, said apertures providing communication between said external space and said thin flat space; and a porous structure disposed within each air inlet aperture and exposed to said thin flat space in a direction of thickness of said thin flat space, and juxtaposed with respect to said first electrode to said direction parallel to the plane of said first planar solid electrolyte body, said porous structure having a second predetermined diffusion resistance to said measurement gas, and maintaining said thin flat space in communication with said external space under said second predetermined diffusion resistance.

* * * * *